(12) United States Patent
Okawa et al.

(10) Patent No.: US 6,197,988 B1
(45) Date of Patent: *Mar. 6, 2001

(54) METHOD FOR PURIFYING 3-METHACRYLOXYPROPYLDIMETHYL-HALOSILANES OR 3-METHACRYLOXYPROPYL METHYLDIHALOSILANES

(75) Inventors: Tadashi Okawa; Ryuzo Mikami, both of Chiba Prefecture (JP)

(73) Assignee: Dow Corning Toray Silicone Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 08/984,482

(22) Filed: Dec. 1, 1997

(30) Foreign Application Priority Data

Dec. 2, 1996 (JP) .................................................. 8-336331

(51) Int. Cl.[7] ........................................................ C07F 7/04
(52) U.S. Cl. .............................................................. 556/440
(58) Field of Search ............................................... 556/440

(56) References Cited

U.S. PATENT DOCUMENTS 5,262,555 * 11/1993 Okawa et al. ..................... 556/440

FOREIGN PATENT DOCUMENTS 5-271248  3/1993 (JP) .
5-301881  4/1993 (JP) .

OTHER PUBLICATIONS

Cameron et al. "Polymerization of poly(dimethylsiloxane)macromers: 1. Copolymerization . . . ", 1985.
English abstract of Hei 5–301881 and Hei 5–271248, 1998.

* cited by examiner

*Primary Examiner*—Paul F. Shaver
(74) *Attorney, Agent, or Firm*—William F. Boley; Jennifer S. Warren

(57) ABSTRACT

A method for purifying 3-methacryloxypropyldimethylhalosilanes or 3-methacryloxypropylmethyldihalosilanes which is characterized by the fact that 1-methyl-2-methacryloxyethyldimethylhalosilanes or 1-methyl-2-methacryloxyethylmethyldihalosilanes contained in products or fractions consisting of 3-methacryloxypropyldimethylhalosilanes or 3-methacryloxypropylmethyldihalosilanes produced by a hydrosilation reaction of allyl methacrylate with dimethylhalosilanes or methyldihalosilanes are decomposed by means of a metal halide which shows the properties of a Lewis acid, after which these compounds are subjected to fractional distillation.

18 Claims, No Drawings

METHOD FOR PURIFYING 3-METHACRYLOXYPROPYLDIMETHYL-HALOSILANES OR 3-METHACRYLOXYPROPYL METHYLDIHALOSILANES

BACKGROUND OF INVENTION

The present invention is a method for purifying 3-methacryloxypropyldimethylhalosilanes or 3-methacryloxypropylmethyldihalosilanes. More specifically, the present invention is a method in which 1-methyl-2-methacryloxyethyldimethylhalosilanes or 1-methyl-2-methacryloxyethylmethyldihalosilanes contained in products or fractions consisting of 3-methacryloxypropyldimethylhalosilanes or 3-methacryloxypropylmethyldihalosilanes produced by a hydrosilation reaction of allyl methacrylate with dimethylhalosilanes or methyl dihalosilanes are decomposed, thus facilitating the fractional distillation of these compounds so that 3-methacryloxypropyldimethylhalosilanes or 3-methacryloxypropylmethyldihalosilanes can be purified to a high purity.

A method in which 3-methacryloxypropyldimethylhalosilanes or 3-methacryloxypropylmethyldihalosilanes are manufactured by subjecting allyl methacrylate and dimethylhalosilanes or methyldihalosilanes to a hydrosilation reaction and then subjecting the resulting products to a fractional distillation is known (see Polymer 26: 437, 1985). When these products are subjected to a fractional distillation a polymerization blocking agent is generally added in order to prevent gelation of the 3-methacryloxypropyldimethylhalosilanes or 3-methacryloxypropylmethyldihalosilanes. It is also known that 3-methacryloxypropyldimethylhalosilanes or 3-methacryloxypropylmethyldihalosilanes can be fractionated with a good yield by using metal halides such as tin chloride, antimony chloride, mercury chloride, copper chloride, bismuth chloride or cobalt chloride as polymerization blocking agents (see Japanese Patent Application Kokai No. 5-271248 and Japanese Patent Application Kokai No. 5-301881).

However, even using fractional distillation, it has not been possible to purify 3-methacryloxypropyldimethylhalosilanes or 3-methacryloxypropylmethyldihalosilanes to a high purity. In investigating the causes of this, the present inventors confirmed that products consisting of 3-methacryloxypropyldimethylhalosilanes or 3-methacryloxypropylmethyldihalosilanes produced by a hydrosilation reaction of allyl methacrylate with dimethylhalosilanes or methyl dihalosilanes, as well as fractions obtained by subjecting such products to fractional distillation, contain small amounts of 1-methyl-2-methacryloxyethyldimethylhalosilanes or 1-methyl-2-methacryloxyethylmethyldihalosilanes which are by-products of the hydrosilation reaction. The boiling points of these 1-methyl-2-methacryloxyethyldimethylhalosilanes or 1-methyl-2-methacryloxyethylmethyldihalosilanes are close to the boiling points of 3-methacryloxypropyldimethylhalosilanes or 3-methacryloxypropylmethyldihalosilanes so that it is difficult to separate these compounds; accordingly, the purity of the 3-methacryloxypropyldimethylhalosilanes or 3-methacryloxypropylmethyldihalosilanes drops. Such 1-methyl-2-methacryloxyethyldimethylhalosilanes or 1-methyl-2-methacryloxyethylmethyldihalosilanes contained in 3-methacryloxypropyldimethylhalosilanes or 3-methacryloxypropylmethyldihalosilanes sometimes create problems. For example, 1-methyl-2-methacryloxyethyldimethylchlorosilane produces impurities such as dimethyldichlorosilane by the following decomposition and interchange reactions:

Formula I

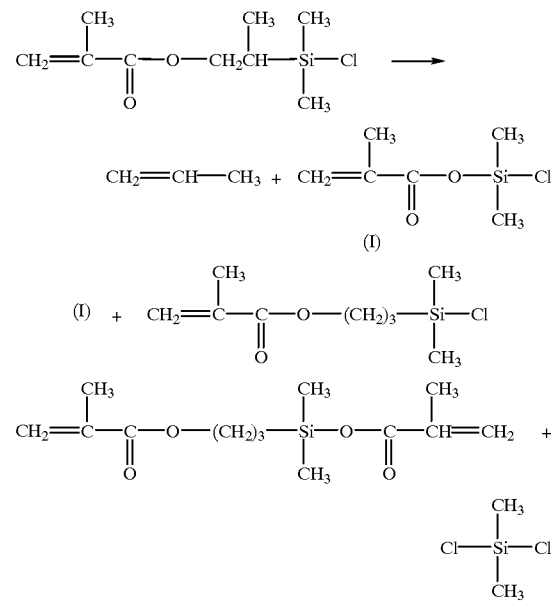

Specifically, the object of the present invention is to provide a method in which 1-methyl-2-methacryloxyethyldimethylhalosilanes or 1-methyl-2-methacryloxyethylmethyldihalosilanes contained in products or fractions consisting of 3-methacryloxypropyldimethylhalosilanes or 3-methacryloxypropylmethyldihalosilanes produced by a hydrosilation reaction of allyl methacrylate with dimethylhalosilanes or methyldihalosilanes are decomposed. Thus, facilitating the fractional distillation of these compounds so that 3-methacryloxypropyldimethylhalosilanes or 3-methacryloxypropylmethyldihalosilanes can be purified to a high purity.

In investigating metal halides as polymerization blocking agents for use in the abovementioned fractional distillation, the present inventors discovered that 1-methyl-2-methacryloxyethyldimethylhalosilanes or 1-methyl-2-methacryloxyethylmethyldihalosilanes contained in products consisting of 3-methacryloxypropyldimethylhalosilanes or 3-methacryloxypropylmethyldihalosilanes are selectively decomposed, and that by thoroughly decomposing these silanes and then subjecting these compounds to a fractional distillation it is possible to purify 3-methacryloxypropyldimethylhalosilanes or 3-methacryloxypropylmethyl dihalosilanes to a high degree of purity. Furthermore, the inventors also discovered that copper (I) chloride and copper (II) chloride can be effectively used in order to perform the abovementioned decomposition reaction under relatively mild conditions, and that copper (I) chloride makes it possible to perform this decomposition reaction more quickly under mild conditions (i.e., at a low temperature) than copper (II) chloride.

SUMMARY OF INVENTION

The present method for purifying 3-methacryloxypropyldimethylhalosilanes or 3-methacryloxypropylmethyldihalosilanes is characterized by the fact that 1-methyl-2-methacryloxyethyldimethylhalosilanes or 1-methyl-2-methacryloxyethylmethyldihalosilanes contained in products or fractions consisting of 3-methacryloxypropyldimethylhalosilanes or 3-methacryloxypropylmethyldihalosilanes produced by a hydrosilation reaction of allyl methacrylate with dimethylhalosilanes or methyldihalosilanes are decomposed by means of a metal halide which shows the properties of a Lewis acid, after which these compounds are subjected to a fractional distillation.

DESCRIPTION OF INVENTION

The present method for purifying 3-methacryloxypropyldimethylhalosilanes or 3-methacryloxypropylmethyldihalosilanes is characterized by the fact that 1-methyl-2-methacryloxyethyldimethylhalosilanes or 1-methyl-2-methacryloxyethylmethyldihalosilanes contained in products or fractions consisting of 3-methacryloxypropyldimethylhalosilanes or 3-methacryloxypropylmethyldihalosilanes produced by a hydrosilation reaction of allyl methacrylate with dimethylhalosilanes or methyldihalosilanes are decomposed by means of a metal halide which shows the properties of a Lewis acid, after which these compounds are subjected to a fractional distillation.

A product consisting of 3-methacryloxypropyldimethylhalosilanes or 3-methacryloxypropylmethyldihalosilanes produced by a hydrosilation reaction of allyl methacrylate with dimethylhalosilanes or methyldihalosilanes, or a fraction obtained by subjecting such a product to a fractional distillation, is used in the purification method of the present invention. Examples of such dimethylhalosilanes or methyldihalosilanes include dimethylfluorosilane, dimethylchlorosilane, dimethylbromosilane, dimethyliodosilane, methyldifluorosilane, methyldichlorosilane, methyldibromosilane and methyldiiodosilane. Dimethylchlorosilane and methyldichlorosilane are especially desirable.

Examples of catalysts which promote this hydrosilation reaction include transition metal type catalysts such as platinum, palladium, rhodium, ruthenium, cobalt, and nickel. Especially desirable are platinum type catalysts such as chloroplatinic acid, alcohol solutions of chloroplatinic acid, ketone solutions of chloroplatinic acid, ether solutions of chloroplatinic acid, olefin complexes of platinum, alkenylsiloxane complexes of platinum, carbonyl complexes of platinum, platinum black, platinum supported on powdered silica, and platinum supported on powdered active carbon.

The use of organic solvents is optional in the abovementioned hydrosilation reaction, and the addition of known polymerization blocking agents is also optional. Examples of such organic solvents include solvents which do not hinder the hydrosilation reaction as exemplified by aromatic solvents such as toluene and xylene and aliphatic solvents such as hexane and heptane. Examples of polymerization blocking agents which can be used include phenothiazine, hindered phenol compounds, amine compounds, quinone compounds, polyphenol derivatives, and oxygen.

Products consisting of 3-methacryloxypropyldimethylhalosilanes or 3-methacryloxypropylmethyldihalosilanes produced by a hydrosilation reaction of allyl methacrylate with dimethylhalosilanes or methyldihalosilanes, as well as fractions obtained by subjecting such products to a fractional distillation, contain small amounts of 1-methyl-2-methacryloxyethyldimethylhalosilanes or 1-methyl-2-methacryloxyethylmethyldihalosilanes which are by-products of the reaction can be used in the present method. In the present method such 1-methyl-2-methacryloxyethyldimethylhalosilanes or 1-methyl-2-methacryloxyethylmethyldihalosilanes are selectively decomposed by means of metal halides which show the properties of a Lewis acid, thus facilitating the purification and separation of 3-methacryloxypropyldimethylhalosilanes or 3-methacryloxypropylmethyldihalosilanes.

Examples of metals contained in the abovementioned metal halides showing the properties of Lewis acids that are useful in the present method include tin, titanium, beryllium, antimony, mercury, copper, bismuth, cobalt, calcium, iron, zinc, cadmium, aluminum, boron, phosphorus, vanadium, chromium, gallium, zirconium, molybdenum, indium, tellurium, tantalum, and tungsten. Examples of the halogens contained in these metal halides include fluorine, chlorine, bromine, and iodine. Examples of such metal halides include tin halides, titanium halides, beryllium halides, antimony halides, mercury halides, copper halides, bismuth halides, cobalt halides, calcium halides, iron halides, zinc halides, and cadmium halides; with copper halides, iron halides, zinc halides, and cobalt halides being most desirable. Especially desirable are copper halides such as copper (I) chloride and copper (II) chloride; iron halides such as iron (II) chloride; zinc halides such as zinc (II) chloride; and cobalt halides such as cobalt (II) chloride. In the case of metal halides with strong Lewis acid properties as exemplified by iron halides such as iron (II) chloride, zinc halides such as zinc (II) chloride, and aluminum halides such as aluminum (II) chloride, there is a danger that bonds between silicon atoms and methyl groups will be broken under harsh conditions, so that even the desired 3-methacryloxypropyldimethylhalosilanes or 3-methacryloxypropylmethyldihalosilanes are decomposed. Accordingly, special attention must be paid to the conditions of the decomposition reaction in such cases. Accordingly, it is desirable that the metal halides used be metal halides with relatively weak Lewis acid properties as exemplified by tin halides such as tin (IV) chloride, titanium halides such as titanium (IV) chloride, beryllium halides such as beryllium (II) chloride, antimony halides such as antimony (V) chloride, mercury halides such as mercury (II) chloride, copper halides such as copper (I) chloride or copper (II) chloride, bismuth halides such as bismuth (II) chloride, cobalt halides such as cobalt (II) chloride, calcium halides such as calcium (II) chloride, or cadmium halides such as cadmium (II) chloride. Copper (I) chloride and/or copper (II) chloride are particularly desirable, and copper (I) chloride is especially desirable since this compound can act relatively efficiently even under mild conditions. Furthermore, since there may be cases where the halogen atoms of the 3-methacryloxypropyldimethylhalosilanes or 3-methacryloxypropylmethyldihalosilanes are interchanged with the halogen atoms of the metal halide used, it is desirable that these halogen atoms be the same.

Examples of the compounds produced when 1-methyl-2-methacryloxyethyldimethylhalosilanes or 1-methyl-2-methacryloxyethylmethyldihalosilanes are decomposed by means of a metal halide showing the properties of a Lewis acid include methacryloxydimethylhalosilanes or methacryloxymethyldihalosilanes, propene, and dimethyldihalosilanes or methyltrihalosilanes. The boiling points of these compounds are lower than the boiling points of 3-methacryloxypropyldimethylhalosilanes or 3-methacryloxypropylmethyldihalosilanes. Accordingly, by subjecting these compounds to a fractional distillation, it is possible to purify 3-methacryloxypropyldimethyl halosilanes or 3-methacryloxypropylmethyldihalosilanes to a high degree of purity.

There are no restrictions on the amounts of such metal halides that are added. The amount of metal halide added depend on the conditions of the decomposition reaction of the 1-methyl-2-methacryloxyethyldimethylhalosilanes or 1-methyl-2-methacryloxyethylmethyldihalosilanes. Generally, however, it is desirable that the amount added be in the range of 0.01 to 20 parts by weight, preferably 0.1 to 10 parts by weight, per 100 parts by weight of the above-mentioned 3-methacryloxypropyldimethylhalosilanes or 3-methacryloxypropylmethyldihalosilanes.

It is desirable that this decomposition reaction be performed without using a solvent. However, the reaction may also be performed in the presence of an organic solvent. Furthermore, although this decomposition reaction may also be performed at room temperature, it is desirable that the reaction be performed with the reaction system heated to a temperature of 50 to 200° C. When 3-methacryloxypropyldimethylhalosilanes or 3-methacryloxypropylmethyldihalosilanes are subjected to a fractional distillation following the completion of this decomposition reaction, a known polymerization blocking agent such as phenothiazine, a hindered phenol compound, an amine compound, a quinone compound, or oxygen may also be added in order to inhibit polymerization of the silanes.

Below, the present method for purifying 3-methacryloxypropyldimethylhalosilanes or 3-methacryloxypropylmethyldihalosilanes will be described in detail in terms of practical examples.

COMPARATIVE EXAMPLE 1

100 g (794 millimoles) of Allyl methacrylate and 0.1 g of 3,5-di-t-butyl-4-hydroxyphenylmethyl dimethylammonium chloride were placed in a four-necked flask equipped with an agitator. Then, a 1,1,3,3-tetramethyl-1,3-divinyldisiloxane complex of platinum was added in an amount providing a ratio of platinum metal to allyl methacrylate (in weight units) of 20 ppm. This system was heated to 90° C. in a nitrogen atmosphere, and a small amount of dimethylchlorosilane was added dropwise. After the initiation of a hydrosilation reaction was confirmed, a total amount of 68.2 g (722 millimoles) of dimethylchlorosilane were added dropwise while the reaction temperature was maintained at 85 to 95° C. by subjecting this system cooling. Following the completion of this dropwise addition the system was agitated for 30 minutes at 80° C., thus producing a product consisting of 3-methacryloxypropyldimethylchlorosilane. This product was analyzed by gas chromatography using a capillary column and an FID detector (hereafter referred to as capillary GLC), and by $^{13}$C-nuclear magnetic resonance analysis. As a result, it was ascertained that this product contained approximately 2 mol % 1-methyl-2-methacryloxyethyldimethylchlorosilane. Next, 0.1 g of 2,6-di-t-butyl-4-methylphenol was added to this product and distillation was performed under reduced pressure at 5 mmHg, thus producing 126.1 g of a fraction with a boiling point of 92 to 105° C. This fraction was subjected to $^{13}$C-nuclear magnetic resonance analysis and $^{29}$Si-nuclear magnetic resonance analysis. It was determined that this product consisted of 93.1% 3-methacryloxypropyldimethylchlorosilane described by formula

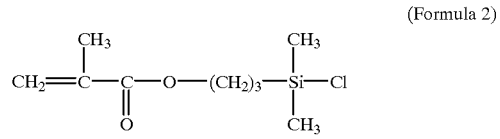

(Formula 2)

2.4% 1-methyl-2-methacryloxyethyldimethylchlorosilane described by formula

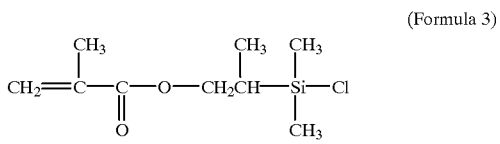

(Formula 3)

1.3% 3-methacryloxypropyl(methacryloxy)dimethylsilane described by formula

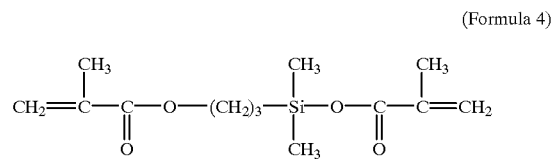

(Formula 4)

0.6% methacryloxydimethylchlorosilane described by formula

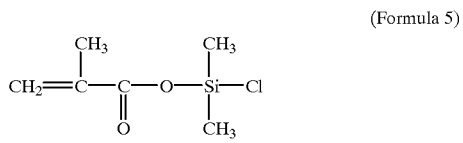

(Formula 5)

0.8% dimethyldichlorosilane, and 1.8% other components.

Practical Example 1

1 g of Copper (II) chloride was added to 66.6 g of the fraction obtained in Comparative Example 1, and this system was heated to 100° C. and agitated in a nitrogen atmosphere. Samples of this reaction mixture were periodically collected, and the 1-methyl-2-methacryloxyethyldimethylchlorosilane content of the reaction mixture was tracked by $^{13}$C-nuclear magnetic resonance analysis. As a result, it was found that this content was 0.37% after 8 hours, 0.2% after 10 hours, and zero after 12 hours. The reaction mixture obtained after 12 hours was subjected to $^{13}$C-nuclear magnetic resonance analysis and $^{29}$Si-nuclear magnetic resonance analysis. It was determined that this reaction mixture consisted of 93.1% 3-methacryloxypropyldimethylchlorosilane, 0.0% 1-methyl-2-methacryloxyethyldimethylchlorosilane, 2.0% 3-methacryloxypropyl (methacryloxy)dimethylsilane, 0.7% methacryloxydimethylchlorosilane, 1.1% dimethyldichlorosilane, and 3.1% other components.

Next, 0.01 g of 2,6-di-t-butyl-4-methylphenol were added to this reaction mixture and the reaction mixture was distilled under reduced pressure at 5 mmHg, thus producing 61 g of a fraction with a boiling point of 97 to 105° C. This fraction was subjected to $^{13}$C-nuclear magnetic resonance analysis and $^{29}$Si-nuclear magnetic resonance analysis. It was determined that this fraction consisted of 98.5% 3-methacryloxypropyldimethylchlorosilane, 0.0% 1-methyl-2-methacryloxyethyldimethylchlorosilane, 0.4% 3-methacryloxypropyl (methacryloxy) dimethylsilane, 0.0% methacryloxydimethylchlorosilane, 0.0% dimethyldichlorosilane, and 1.1% other components.

COMPARATIVE EXAMPLE 2

The fraction obtained in Comparative Example 1 was heated and agitated for 12 hours at 100° C. in a dry air atmosphere. When this fraction was subjected to $^{13}$C-nuclear magnetic resonance analysis and $^{29}$Si-nuclear magnetic resonance analysis, there was no change in the composition and no decomposition of 1-methyl-2-methacryloxyethyldimethylchlorosilane occurred.

Practical Example 2

0.15 g of Iron (II) chloride was added to 10 g of the fraction obtained in Comparative Example 1, and this system was heated and agitated for 8 hours at 100° C. in an air atmosphere. When this reaction mixture was analyzed by $^{13}$C-nuclear magnetic resonance analysis it was confirmed that no 1-methyl-2-methacryloxyethyldimethylchlorosilane was contained in the reaction mixture. Next, 0.01 g of 2,6-di-t-butyl-4-methylphenol was added to this reaction mixture and the reaction mixture was distilled under reduced pressure at 5 mmHg, thus producing a fraction with a boiling point of 97 to 105° C. This fraction was subjected to $^{13}$C-nuclear magnetic resonance analysis and $^{29}$Si-nuclear magnetic resonance analysis. As a result, it was confirmed that this fraction had a composition similar to that described in Practical Example 1.

Practical Example 3

0.15 g of Zinc (II) chloride was added to 10 g of the fraction obtained in Comparative Example 1 and this system was heated and agitated for 8 hours at 100° C. in an air atmosphere. When this reaction mixture was analyzed by $^{13}$C-nuclear magnetic resonance analysis it was confirmed that no 1-methyl-2-methacryloxyethyldimethylchlorosilane was contained in the reaction mixture. Next, 0.01 g of 2,6-di-t-butyl-4-methylphenol was added to this reaction mixture and the reaction mixture was distilled under reduced pressure at 5 mmHg, thus producing a fraction with a boiling point of 97 to 105° C. This fraction was subjected to $^{13}$C-nuclear magnetic resonance analysis and $^{29}$Si-nuclear magnetic resonance analysis. As a result, it was confirmed that this fraction had a composition similar to that described in Practical Example 1.

Practical Example 4

0.15 g of Cobalt (II) chloride was added to 10 g of the fraction obtained in Comparative Example 1 and this system was heated and agitated for 8 hours at 100° C. in an air atmosphere. When this reaction mixture was analyzed by $^{13}$C-nuclear magnetic resonance analysis it was confirmed that no 1-methyl-2-methacryloxyethyldimethylchlorosilane was contained in the reaction mixture. Next, 0.01 g of 2,6-di-t-butyl-4-methylphenol was added to this reaction mixture and the reaction mixture was distilled under reduced pressure at 5 mmHg, thus producing a fraction with a boiling point of 97 to 105° C. This fraction was subjected to $^{13}$C-nuclear magnetic resonance analysis and $^{29}$Si-nuclear magnetic resonance analysis. As a result, it was confirmed that this fraction had a composition similar to that described in Practical Example 1.

Practical Example 5

100 g (794 millimoles) of Allyl methacrylate and 0.1 g of 3,5-di-t-butyl-4-hydroxyphenylmethyl dimethylammonium chloride were placed in a four-necked flask equipped with an agitator. Then a 1,1,3,3-tetramethyl-1,3-divinyldisiloxane complex of platinum was added in an amount providing a ratio of platinum metal to allyl methacrylate (in weight units) of 20 ppm. This system was heated to 90° C. in a nitrogen atmosphere and a small amount of dimethylchlorosilane was added dropwise. After the initiation of a hydrosilation reaction was confirmed, a total amount of 68.2 g (722 millimoles) of dimethylchlorosilane was added dropwise while the reaction temperature was maintained at 85 to 95° C. by subjecting this system to cooling. Following the completion of this dropwise addition, the system was agitated for 30 minutes at 80° C., thus producing a product consisting of 3-methacryloxypropyldimethylchlorosilane. This product was analyzed by capillary GLC and $^{13}$C-nuclear magnetic resonance analysis. It was determined that this product contained approximately 2 mol % 1-methyl-2-methacryloxyethyldimethylchlorosilane.

Next, 0.55 g (5.58 millimoles) of copper (I) chloride was added to 50 g of this product and this system was heated and agitated for 3 hours at 100° C. Afterward, when this product was analyzed by capillary GLC, it was ascertained that 45% of the 1-methyl-2-methacryloxyethyldimethylchlorosilane had been decomposed. Furthermore, when this product was again analyzed by capillary GLC after the system had been heated and agitated for an additional 3 hours at 100° C., it was ascertained that 97% of the 1-methyl-2-methacryloxyethyldimethylchlorosilane had been decomposed. Next, 0.03 g of 2,6-di-t-butyl-4-methylphenol was added to this product, after which the product was distilled under reduced pressure at 5 mmHg and a fraction with a boiling point of 92 to 105° C. was collected. This fraction was subjected to $^{13}$C-nuclear magnetic resonance analysis and $^{29}$Si-nuclear magnetic resonance analysis. It was determined that this fraction consisted of 98.9% 3-methacryloxypropyldimethylchlorosilane, 0.0% 1-methyl-2-methacryloxyethyldimethylchlorosilane, 0.3% 3-methacryloxypropyl(methacryloxy)dimethylsilane, 0.0% methacryloxydimethylchlorosilane, 0.0% dimethyldichlorosilane, and 0.8% other components.

COMPARATIVE EXAMPLE 3

100 g (794 millimoles) of Allyl methacrylate and 0.1 g of 3,5-di-t-butyl-4-hydroxyphenylmethyl dimethylammonium chloride were placed in a four-necked flask equipped with an agitator. Then, a 1,1,3,3-tetramethyl-1,3-divinyldisiloxane complex of platinum was added in an amount providing a ratio of platinum metal to allyl methacrylate (in weight units) of 20 ppm. This system was heated to 90° C. in a nitrogen atmosphere and a small amount of dimethylchlorosilane was added dropwise. After the initiation of a hydrosilation reaction was confirmed, a total amount of 68.2 g (722 millimoles) of dimethylchlorosilane was added dropwise while the reaction temperature was maintained at 85 to 95° C. by subjecting this system to cooling. Following the completion of this dropwise addition the system was agitated for 30 minutes at 80° C., thus producing a product consisting of 3-methacryloxypropyldimethylchlorosilane. Next, 1.0 g of copper (II) chloride and 0.1 g of 2,6-di-t-butyl-4-methylphenol were added to this product, after which the product was distilled under reduced pressure at 5 mmHg and a fraction with a boiling point of 92 to 105° C. was collected. This fraction was subjected to $^{13}$C-nuclear magnetic resonance analysis and $^{29}$Si-nuclear magnetic resonance analysis. It was determined that this fraction consisted of 96.1% 3-methacryloxypropyldimethylchlorosilane, 1.4% 1-methyl-2-methacryloxyethyldimethylchlorosilane, 0.8% 3-methacryloxypropyl(methacryloxy)dimethylsilane, 0.2% methacryloxydimethylchlorosilane, 0.2% dimethyldichlorosilane, and 1.3% other components.

We claim:

1. A method for purifying 3-metacryloxypropyldimethylhalosilanes comprising contacting a mixture comprising 3-methacryloxypropyldimethyhalosilane and at least 1 mole percent 1-methyl-2-methacryloxyethyldimethylhalosilane with a Lewis acid metal halide to effect decomposition of the 1-methyl-2-methacryloxyethyldimethylhalosilane until the 1-methyl-2-methacryloxyethyldimethylhalosilane comprises less than 1 mole percent of the mixture.

2. A method according to claim 1, where the Lewis acid metal halide is selected from the group consisting of copper halides, iron halides, zinc halides, and cobalt halides.

3. A method according to claim 1, where the Lewis acid metal halide is selected from the group consisting of copper(I) chloride, copper(II) chloride, iron(II) chloride, zinc(II) chloride, and cobalt(II) chloride.

4. A method according to claim 1, where the Lewis acid metal halide is selected from the group consisting of tin(IV) chloride, titanium(IV) chloride, beryllium(II) chloride, antimony(V) chloride, mercury(II) chloride, copper(I) chloride, copper(II) chloride, bismuth(II) chloride, cobalt(II) chloride, calcium(II) chloride, and cadmium(II) chloride.

5. A method according to claim 1, where the Lewis acid metal halide is selected from the group consisting of copper(I) chloride and copper(II) chloride.

6. A method according to claim 1, where the Lewis acid metal halide is copper(I) halide.

7. A method according to claim 1, where the Lewis acid metal halide is present at a concentration within a range of 0.01 to 20 parts by weight per 100 parts by weight of the 3-methacryloxypropyldimethylhalosilane.

8. A method according to claim 1, where the Lewis acid metal halide is present at a concentration in the range of 0.1 to 10 parts by weight per 100 parts by weight of the 3-methacryloxypropyldimethylhalosilane.

9. A method according to claim 1, where the contact of the mixture with the Lewis acid metal halide is effected at a temperature of 50 to 200° C.

10. A method for purifying 3-metacryloxypropylmethyldihalosilanes comprising contacting a mixture comprising 3-methacryloxypropylmethyldihalosilane and at least 1 mole percent 1-methyl-2-methacryloxyethylmethyldihalosilane with a Lewis acid metal halide to effect decomposition of the 1-methyl-2-methacryloxyethylmethyldihalosilane until the 1-methyl-2-methacryloxyethylmethyldihalosilane comprises less than 1 mole percent of the mixture.

11. A method according to claim 10, where the Lewis acid metal halide is selected from the group consisting of copper halides, iron halides, zinc halides, and cobalt halides.

12. A method according to claim 10, where the Lewis acid metal halide is selected from the group consisting of copper(I) chloride, copper(II) chloride, iron(II) chloride, zinc(II) chloride, and cobalt(II) chloride.

13. A method according to claim 10, where the Lewis acid metal halide is selected from the group consisting of tin(IV) chloride, titanium(IV) chloride, beryllium(II) chloride, antimony(V) chloride, mercury(II) chloride, copper(I) chloride, copper(II) chloride, bismuth(II) chloride, cobalt(II) chloride, calcium(II) chloride, and cadmium(II) chloride.

14. A method according to claim 10, where the Lewis acid metal halide is selected from the group consisting of copper(I) chloride and copper(II) chloride.

15. A method according to claim 10, where the Lewis acid metal halide is copper(I) halide.

16. A method according to claim 10, where the Lewis acid metal halide is present at a concentration within a range of 0.01 to 20 parts by weight per 100 parts by weight of the 3-methacryloxypropylmethyldihalosilane.

17. A method according to claim 10, where the Lewis acid metal halide is present at a concentration in the range of 0.1 to 10 parts by weight per 100 parts by weight of the 3-methacryloxypropylmethyldihalosilane.

18. A method according to claim 10, where the contact of the mixture with the Lewis acid metal halide is effected at a temperature of 50 to 200° C.

* * * * *